(12) United States Patent
Kihiczak

(10) Patent No.: US 11,857,381 B1
(45) Date of Patent: Jan. 2, 2024

(54) ANATOMICAL LOCALIZATION DEVICE AND METHOD OF USE

(71) Applicant: Danylo Kihiczak, Los Angeles, CA (US)

(72) Inventor: Danylo Kihiczak, Los Angeles, CA (US)

( * ) Notice: Subject to any disclaimer, the term of this patent is extended or adjusted under 35 U.S.C. 154(b) by 0 days.

(21) Appl. No.: 18/138,780

(22) Filed: Apr. 25, 2023

(51) Int. Cl.
*A61B 90/00* (2016.01)

(52) U.S. Cl.
CPC ........ *A61B 90/39* (2016.02); *A61B 2090/395* (2016.02); *A61B 2090/3966* (2016.02)

(58) Field of Classification Search
CPC .............. A61B 90/39; A61B 2090/392; A61B 2090/395; A61B 2090/3933; A61B 2090/3966
USPC ....................................... 401/6, 195
See application file for complete search history.

(56) References Cited

U.S. PATENT DOCUMENTS

| 2,395,924 | A | 1/2001 | Bedell | |
|---|---|---|---|---|
| 7,097,357 | B2 | 8/2006 | Johnson | |
| 9,186,225 | B1 * | 11/2015 | Pettis | A61B 90/39 |
| 9,375,189 | B1 * | 6/2016 | Alsahhaf | A61B 6/107 |
| 10,959,803 | B2 * | 3/2021 | Halpert | B43K 29/08 |
| 11,399,895 | B2 | 8/2022 | Soper | |
| 2019/0110857 | A1 * | 4/2019 | Pettis | A61B 90/39 |
| 2019/0282304 | A1 | 9/2019 | Sato | |
| 2020/0155107 | A1 | 5/2020 | Spencer | |
| 2021/0353245 | A1 | 5/2021 | Hudon | |
| 2022/0031263 | A1 | 2/2022 | Bertram | |
| 2022/0092800 | A1 | 3/2022 | Toporek | |

* cited by examiner

*Primary Examiner* — Jennifer C Chiang

(57) ABSTRACT

An anatomical localization device for marking an entry point on the skin over an anatomical target includes an elongate handle, which can be grasped in a hand of a user proximate to its first end. A marker assembly, which is attached to a second end of the elongate handle, can be selectively actuated to impart a mark to skin of a subject. The marker assembly comprises a plastic composite so that the marker assembly is radiolucent. An indicator, which is attached to the marker assembly, is radiopaque and thus is radiographically visualized. The user can manipulate the elongate handle to motivate the marker assembly across an anatomical region of a subject who is being radiographically visualized. The indicator thus can be localized over an anatomical target, such that selective actuation of the marker assembly marks the skin over the anatomical target.

20 Claims, 8 Drawing Sheets

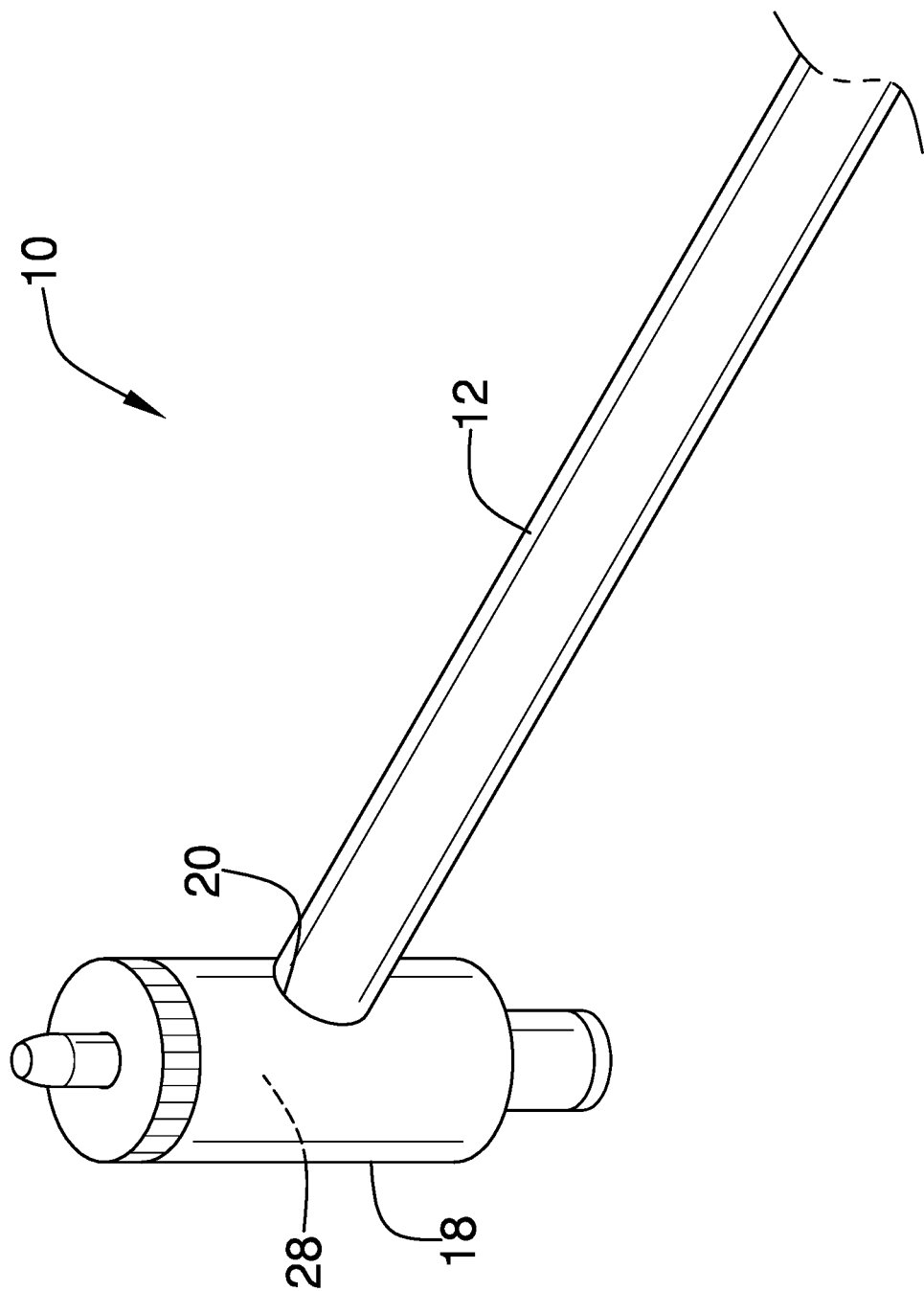

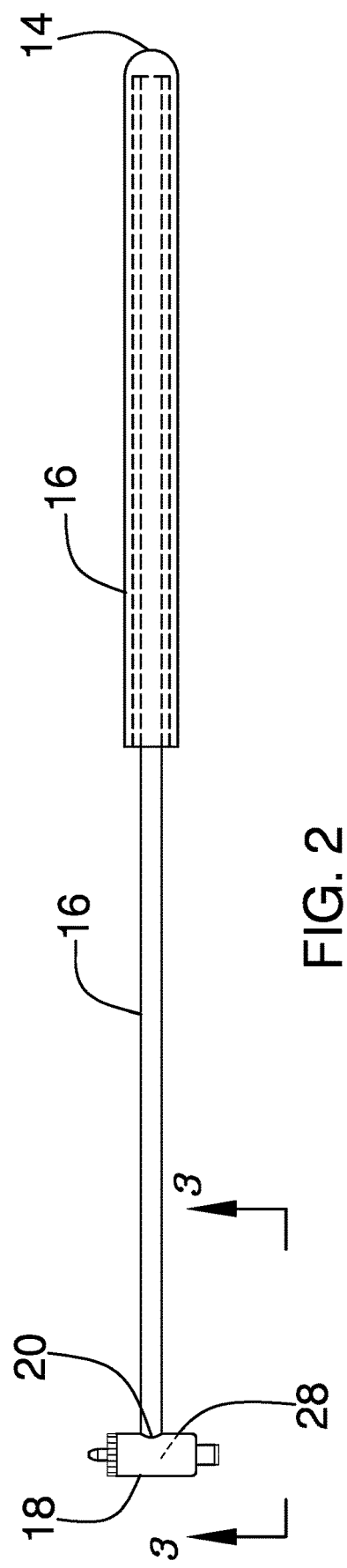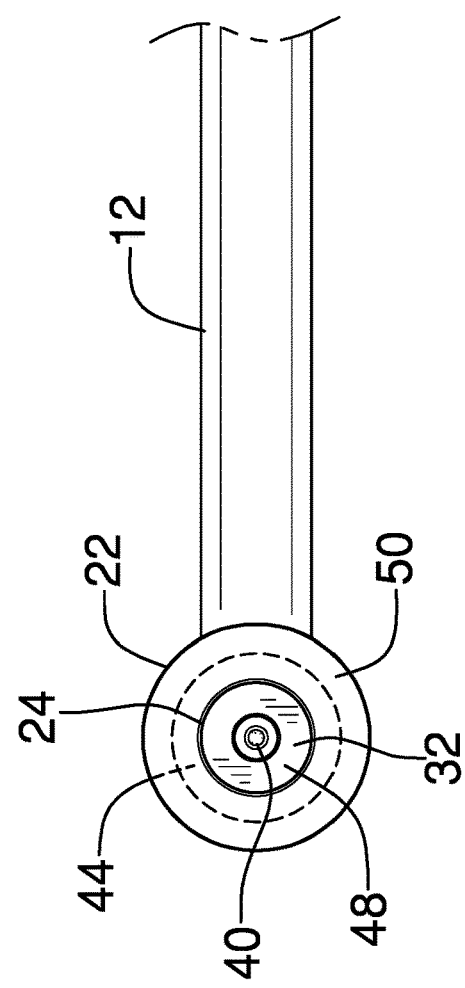

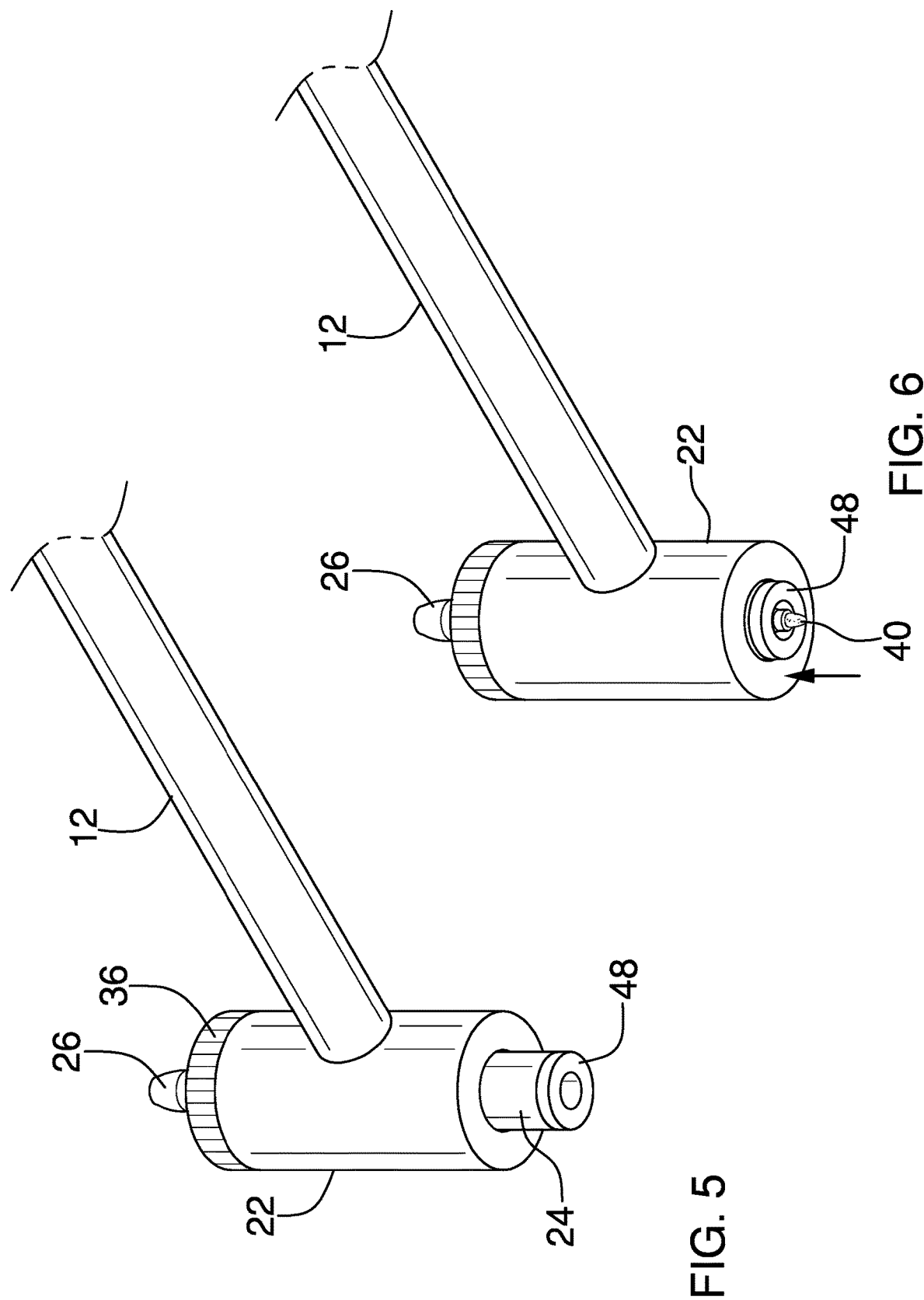

ANATOMICAL LOCALIZATION DEVICE AND METHOD OF USE

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION

(1) Field of the Invention

The disclosure relates to anatomical markers and more particularly pertains to a new anatomical marker for marking an entry point on the skin over an anatomical target. The present invention discloses an anatomical marker which is substantially radiolucent and which can be used during radiographic procedures for real time marking of one or more targets.

(2) Description of Related Art Including Information Disclosed Under 37 CFR 1.97 and 1.98

The prior art relates to anatomical markers, which may comprise fluoroscopic imaging devices with integrated lasers used to project a mark onto a subject. Related prior art includes radiopaque trackers that are attachable to subjects, radiopaque markers used in surgical procedures, such as stent placement, radiopaque markers affixed to intravascular devices, and radiopaque markers attached to flat panel detectors of X-ray devices. The prior art does not disclose an anatomical marker enabling real-time radiographically guided marking of skin over an anatomical target.

Currently, when using radiologic imaging to localize anatomy, we will put a metal object, such as scissors, forceps, or the like, on a subject proximate to an anatomical target, such as an entry point for a needle, an incision line, or the like. The target area then is visualized to show the metal object's position relative to the anatomical target. Should the metal object overlie the anatomical target, a marking pen can be used to mark the site. Should the metal object not overlie the anatomical target, is moved and imaging is repeated. This process is repeated until the metal object overlies the anatomical target. This localization technique is not ideal as it is time consuming, exposes the subject to repeated doses of radiation, and is subject to error and shifting of the metal object may occur during movement of equipment.

(h) BRIEF SUMMARY OF THE INVENTION

An embodiment of the disclosure meets the needs presented above by generally comprising an elongate handle, which is configured to be grasped in a hand of a user proximate to its first end. A marker assembly is attached to a second end of the elongate handle and is configured for selective actuation to impart a mark to skin of a subject. The marker assembly comprises a plastic composite so that the marker assembly is radiolucent. An indicator, which is attached to the marker assembly, is radiopaque and thus configured to be radiographically visualized. The elongate handle is configured to be manipulated by the user to motivate the marker assembly across an anatomical region of a subject who is being radiographically visualized. The indicator thus can be localized over an anatomical target, enabling the user to selectively actuate the marker assembly to mark the skin over the anatomical target.

Another embodiment of the disclosure includes a radiographically guided method of marking an anatomical target. Provision steps of the method entail providing a radiographic imaging device and providing an anatomical localization device, according to the disclosure above. Use steps of the method are positioning a subject for imaging, grasping the elongate handle and positioning the marker assembly on the skin of the subject proximate to the anatomical target, actuating the radiographic imaging device, manipulating the elongate handle to position the indicator over the anatomical target, and actuating the marker assembly to mark the skin over the anatomical target.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 1 is a top isometric perspective view of an anatomical localization device according to an embodiment of the disclosure.

FIG. 2 is a side view of an embodiment of the disclosure.

FIG. 3 is a bottom view of an embodiment of the disclosure.

FIG. 5 is a bottom isometric perspective view of an embodiment of the disclosure.

FIG. 6 is a bottom isometric perspective view of an embodiment of the disclosure.

(j) DETAILED DESCRIPTION OF THE INVENTION

Figure 4:
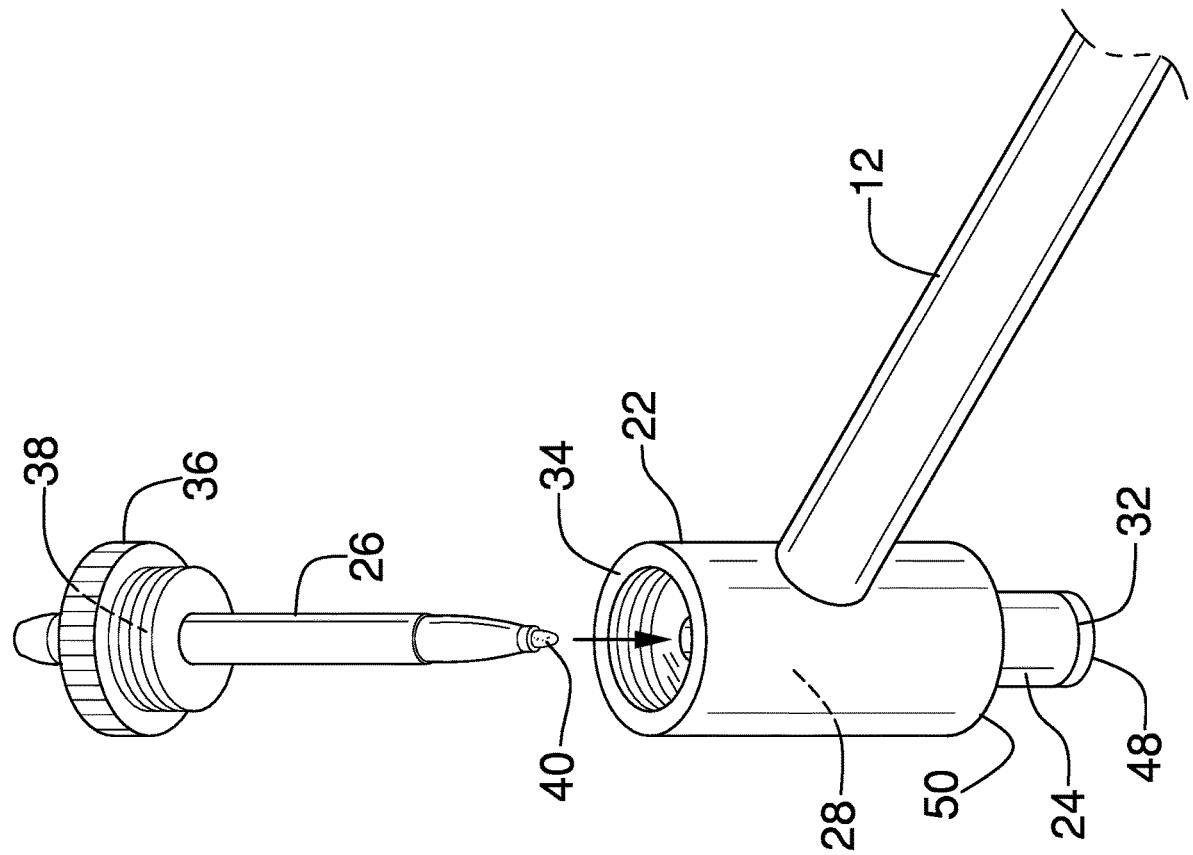
FIG. 4 is an exploded view of an embodiment of the disclosure.

With reference now to the drawings, and in particular to FIGS. 1 through 10 thereof, a new anatomical marker embodying the principles and concepts of an embodiment of the disclosure and generally designated by the reference numeral 10 will be described.

As best illustrated in FIGS. 1 through 10, the anatomical localization device 10 generally comprises an elongate handle 12, which is configured to be grasped in a hand of a user proximate to its first end 14. As is shown in FIG. 2, the elongate handle 12 comprises a plurality of nested sections 16 and thus is selectively extensible. The plurality of nested sections 16 may comprise two nested sections 16, which provides for sufficient compaction of the anatomical localization device 10 to facilitate storage when not in use, or more than two nested sections 16.

A marker assembly 18 is attached to a second end 20 of the elongate handle 12 and is configured for selective actuation to impart a mark to skin of a subject. The marker assembly 18 and comprises plastic composite so that the marker assembly 18 is radiolucent. The marker assembly 18 may comprise, for example, polyetherimide, polycarbonate, polyethylene, polypropylene, polyoxymethylene, or the like. The elongate handle 12 may be comprised of any conventional rigid material providing sufficient stability when using the marker assembly 18, particularly as the elongated handle 12 need not be radiolucent. Thus, while plastics may be utilized, other materials such as stainless steel, titanium or other metals may be preferred for their durability and mass.

Figure 7:
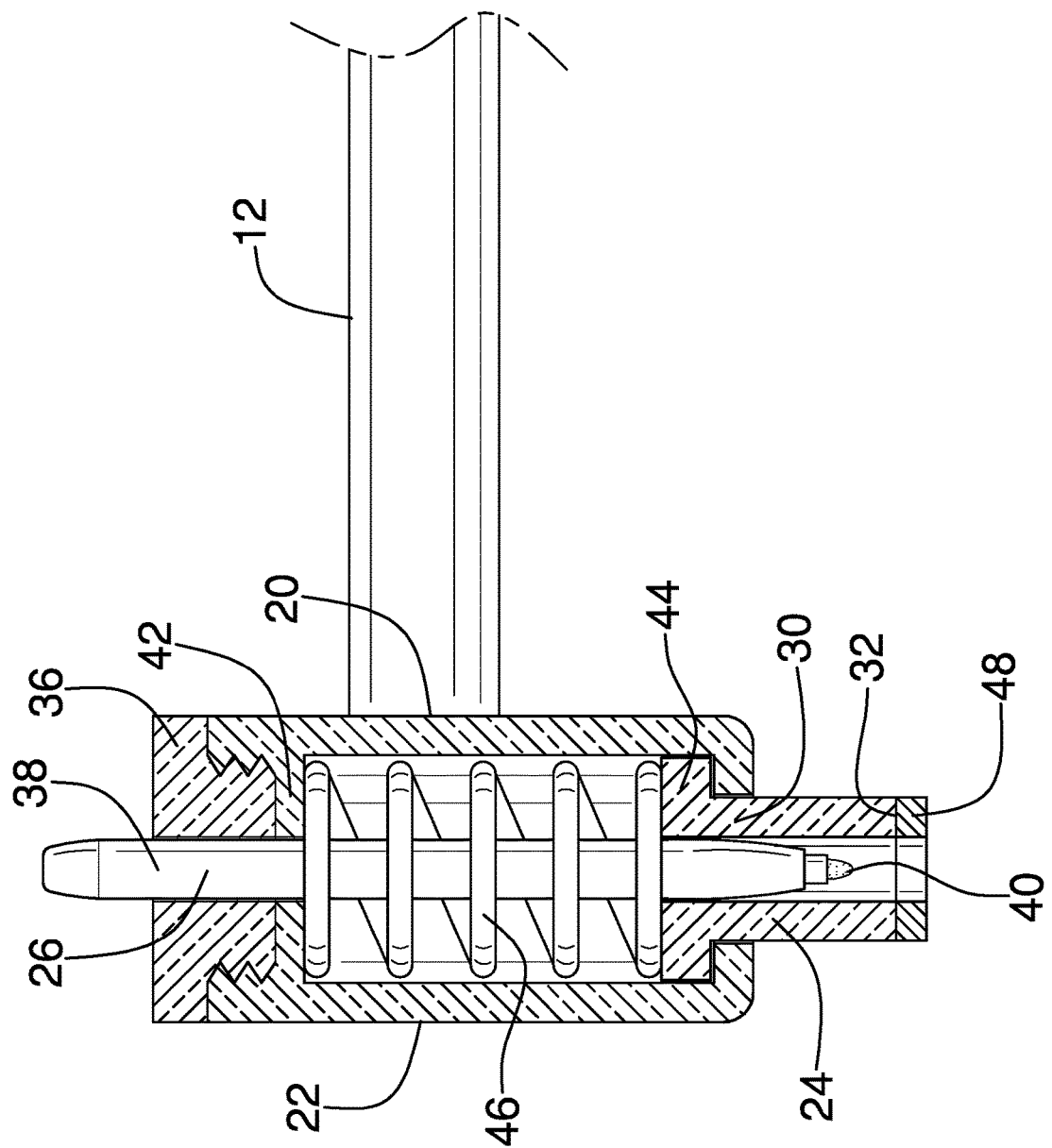
FIG. 7 is a cross-sectional view of an embodiment of the disclosure.
Figure 8:
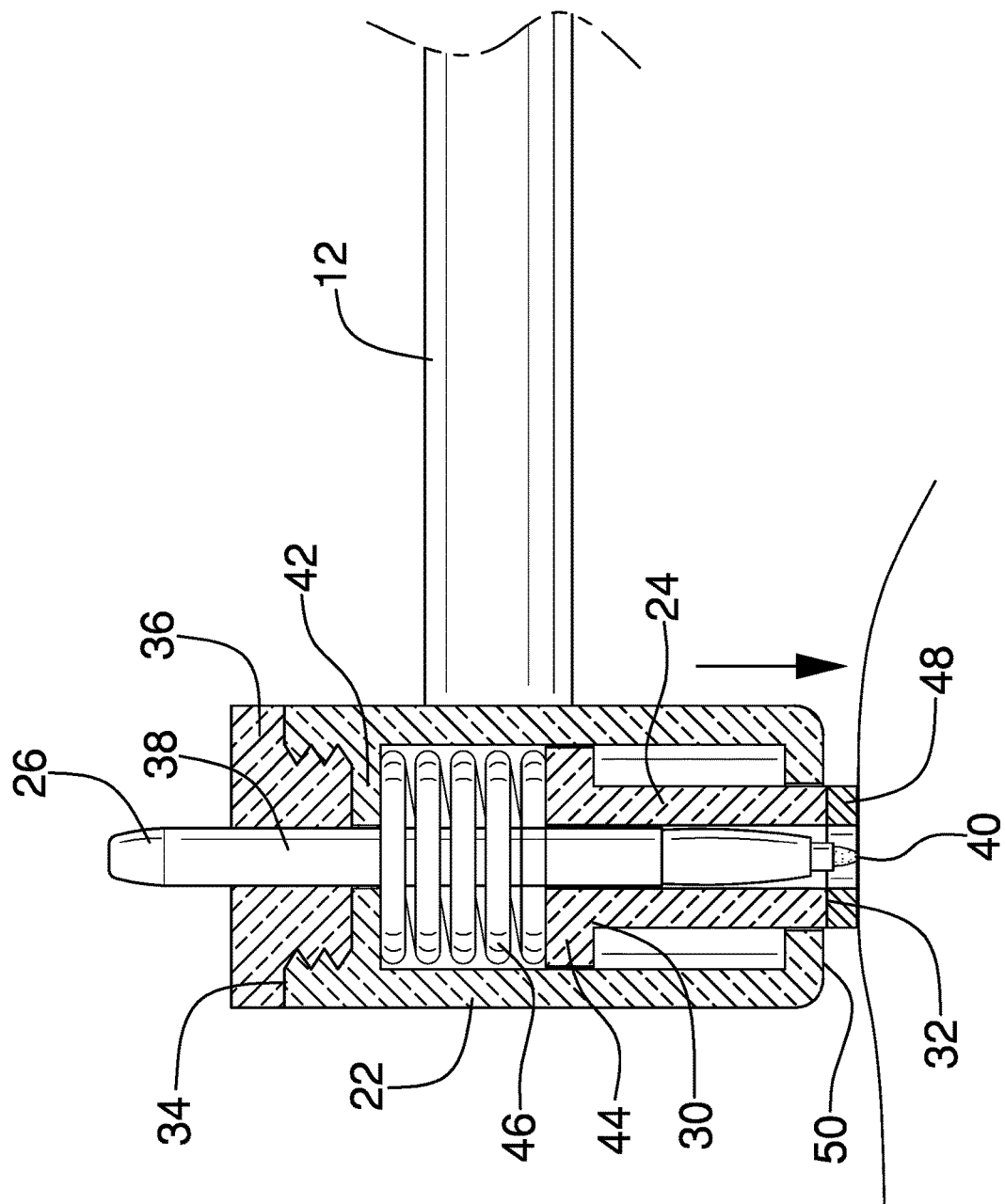
FIG. 8 is a cross-sectional view of an embodiment of the disclosure.
Figure 9:
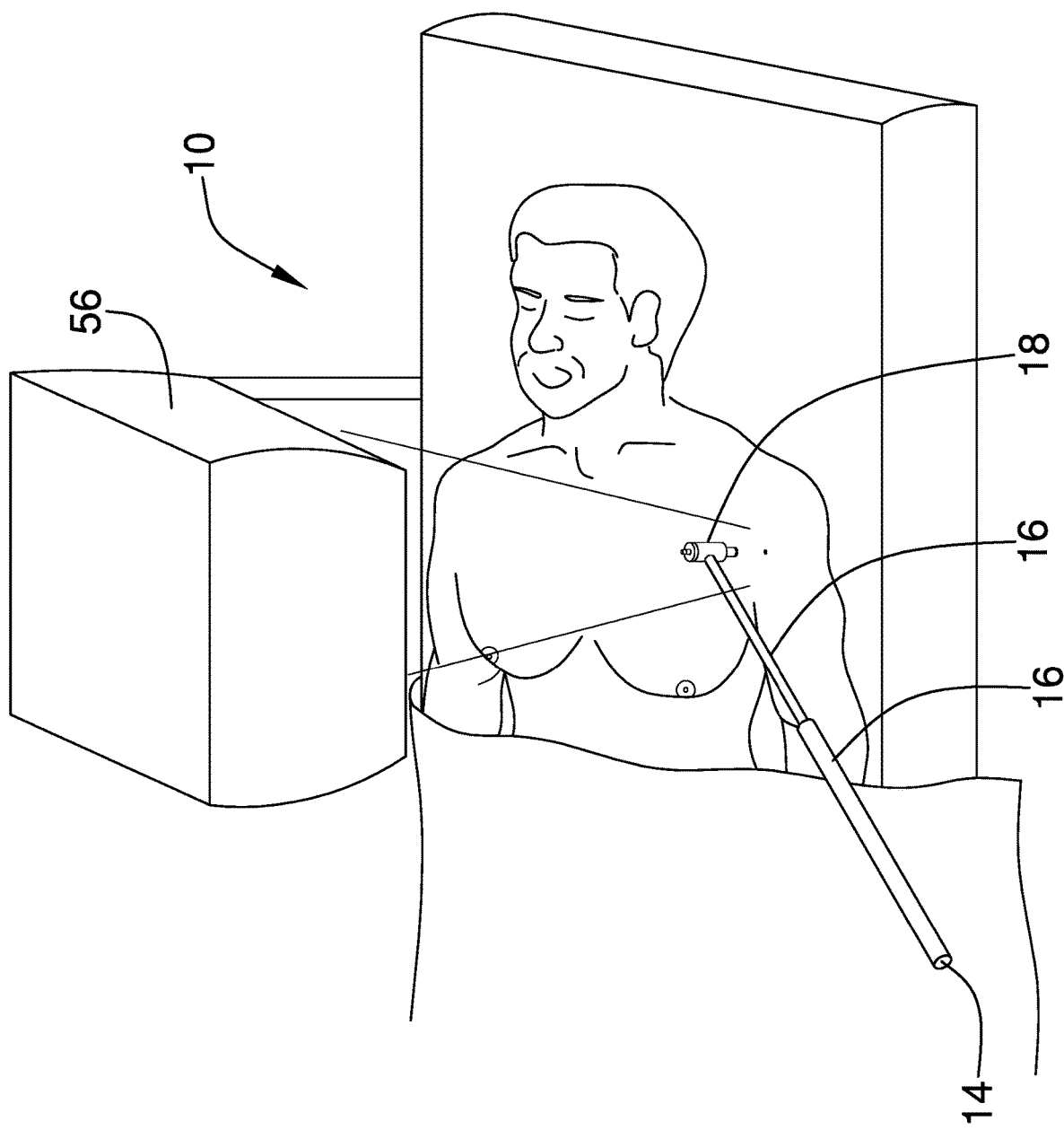
FIG. 9 is an in-use view of an embodiment of the disclosure.
Figure 10:
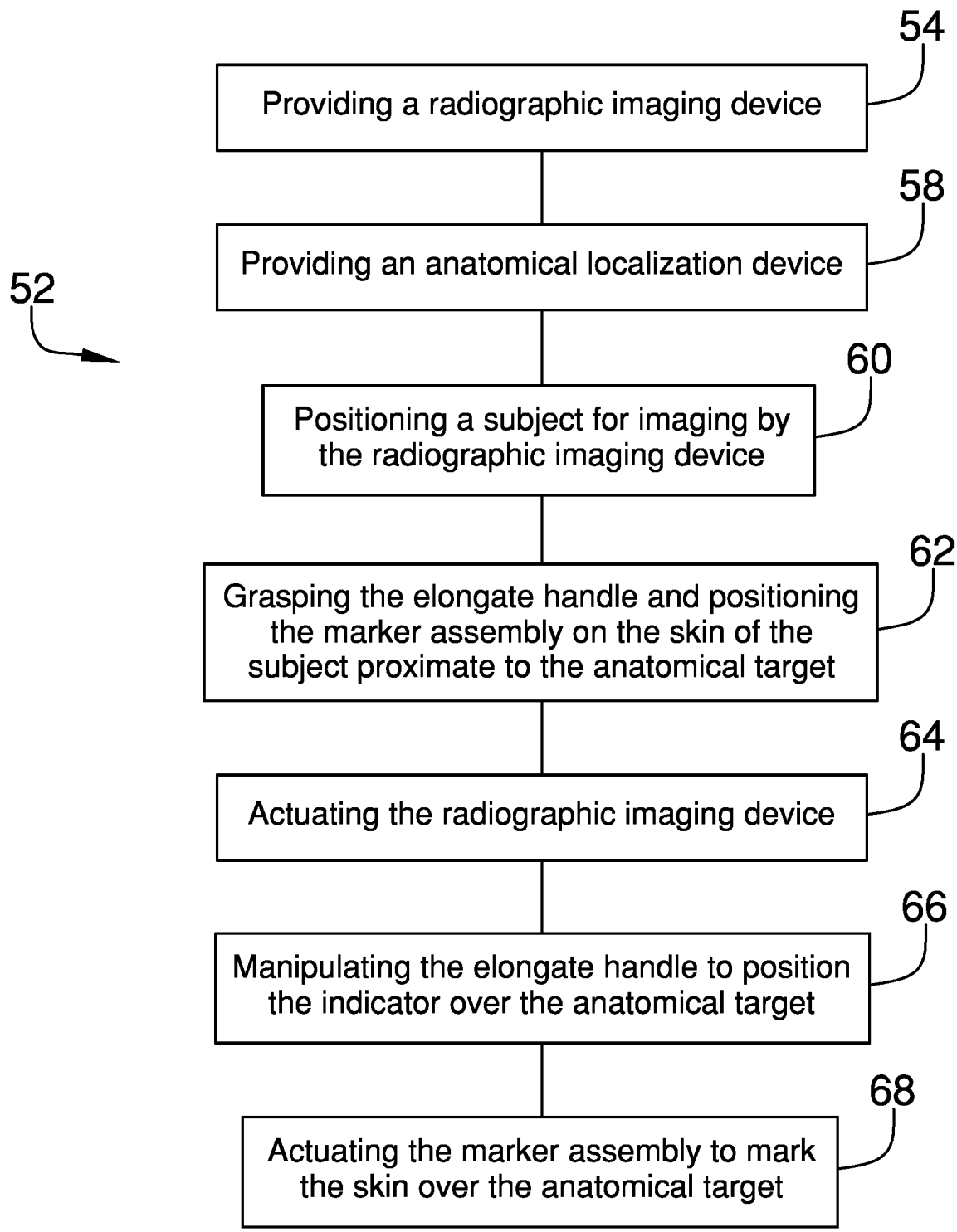
FIG. 10 is a flow diagram for a method utilizing an embodiment of the disclosure.

One configuration anticipated for the marker assembly 18 is depicted in FIGS. 7 and 8, wherein the marker assembly 18 comprises a first tube 22, a second tube 24, a marking pen 26, and a biaser 28. The second tube 24 is slidably attached to the first tube 22, with an upper limit 30 of the second tube 24 being positioned within the first tube 22 and a lower limit 32 of the second tube 24 being external to the first tube 22. The first tube 22 and the second tube 24 may be cylindrical, as is shown in FIGS. 1-5. As shaping of the first tube 22 and the second tube 24 are not critical to functioning of the anatomical localization device 10, alternative shaping is anticipated by the present invention, such as, but not limited to, cuboid, polyhedric, or the like.

The first tube 22 is internally threaded adjacent to its upper end 34. A cap 36 is selectively threadedly attachable to the first tube 22 to close the upper end 34. A channel 38 extends axially through the cap 36. As is shown in FIG. 6, the elongate handle 12 extends substantially radially from the first tube 22. The present invention also anticipates the elongate handle 12 extending angularly from the first tube 22, for example, toward the upper end 34 of the first tube 22. As will become apparent, angling of the elongate handle 12 toward the upper end 34 of the first tube 22 may facilitate pressing of the marker assembly 18 against skin of a subject.

The marking pen 26, which is attached to and positioned substantially within the first tube 22, extends also into the second tube 24. The marking pen 26 is circumferentially complementary to and positioned through the channel 38 so that the marking pen 26 is frictionally attached to the cap 36. The present invention also anticipates the marking pen 26 being attached to the cap 36 or to the first tube 22 by other attachment means, such as, but not limited to, adhesives, clips, or the like.

The biaser 28 is attached to the first tube 22 and is operationally engaged to the second tube 24 so that the second tube 24 is biased to a first position, as is shown in FIGS. 5 and 7, wherein the second tube 24 extends from the first tube 22 past a tip 40 of the marking pen 26. With the second tube 24 in the first position, the tip 40 is prevented from marking the skin of the subject. The second tube 24 is configured to be pressed against the skin over an anatomical target, such as a shoulder joint, knee joint, or the like, such that the second tube 24 retracts into the first tube 22, as is shown in FIGS. 6 and 8, and the marking pen 26 imparts a mark to the skin.

As is shown in FIGS. 7 and 8, a first ring 42 is attached to and positioned within the first tube 22 proximate to its upper end 34. A second ring 44 is attached to and extends radially from the upper limit 30 of the second tube 24. The biaser 28 comprises a spring 46, which is positioned in the first tube 22 between the first ring 42 and the second ring 44. The spring 46 is configured to be tensioned upon pressing of the lower limit 32 of the second tube 24 against the skin of the subject and to rebound upon lifting of the marker assembly 18 from the skin. The present invention anticipates other configurations of the marker assembly 18, such as, but not limited to, the marking pen 26 being spring loaded and selectively actuatable, a stamp actuated by a trigger attached to the elongate handle 12 proximate to its first end 14, or the like.

An indicator 48, which is attached to the marker assembly 18, is radiopaque and thus configured to be radiographically visualized. The indicator 48 comprises barium sulfate, aluminum, stainless steel, titanium, gold, platinum, tantalum, or the like. As is shown in FIGS. 5 and 6, the indicator 48 is attached to the lower limit 32 of the second tube 24. The present invention also anticipates the indicator 48 being attached to a lower end 50 of the first tube 22.

The elongate handle 12 is configured to be manipulated by the user to motivate the marker assembly 18 across an anatomical region of a subject who is being radiographically visualized. Such radiographic imaging is performed routinely using fluoroscopy, radiography, and X-ray computed tomography. The indicator 48 thus can be localized over an anatomical target, enabling the user to selectively actuate the marker assembly 18 to mark the skin over the anatomical target. The elongate handle 12 allows the user to utilize the marker assembly 18 without positioning their hand within an area being exposed to the radiological imaging. The fully extended length of elongate handle 12 will typically be up to about 24.0 inches.

In use, the anatomical localization device 10 enables a radiographically guided method of marking an anatomical target 52. The method 52 comprises a first provision step 54, which entails providing a radiographic imaging device 56. A second provision step 58 of the method 52 is providing an anatomical localization device 10, according to the specification above. A first use step 60 of the method 52 is positioning a subject for imaging by the radiographic imaging device 56. A second use step 62 of the method 52 is grasping the elongate handle 12 and positioning the marker assembly 18 on the skin of the subject proximate to the anatomical target. A third use step 64 of the method 52 is actuating the radiographic imaging device. A fourth use step 66 of the method 52 is manipulating the elongate handle 12 to position the indicator 48 over the anatomical target. The elongate handle 12, in being elongated, allows the user to manipulate the marking assembly 18 with little or no risk of radiation exposure from the radiographic imaging device 56. A fifth use step 68 of the method 52 is actuating the marker assembly 18 to mark the skin over the anatomical target.

With the marker assembly 18 comprising a first tube 22, a second tube 24, a marking pen 26, and a biaser 28, as described in the specification above, the step of actuating the marker assembly 18 comprises application of a force to the elongate handle 12 to press the second tube 24 against the skin of the subject. In so doing, the second tube 24 is retracted into the first tube 22 and the tip 40 of the marking pen 26 contacts the skin over the anatomical target.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An anatomical localization device comprising:
   an elongate handle configured for being grasped in a hand of a user proximate to a first end of the elongate handle;
   a marker assembly attached to a second end of the elongate handle and being configured for selective actuation for imparting a mark to skin of a subject, the marker assembly comprising plastic composite, such that the marker assembly is radiolucent, the marker assembly being actuated in a linear direction by pressure on the marker assembly to produce the mark on the skin aligned with the direction of pressure applied to the marker assembly; and
   an indicator attached to the marker assembly, the indicator being radiopaque, wherein the indicator is configured for being radiographically visualized, wherein the elongate handle is configured for being manipulated by the user for motivating the marker assembly across an anatomical region of a subject being radiographically visualized for localizing the indicator over an anatomical target, enabling the user for selectively actuating the marker assembly for marking the skin over the anatomical target.

2. The anatomical localization device of claim 1, wherein the elongate handle comprises a plurality of nested sections, such that the elongate handle is selectively extensible.

3. The anatomical localization device of claim 2, wherein the plurality of nested sections comprises two nested sections.

4. The anatomical localization device of claim 1, wherein the marker assembly comprise polyetherimide, polycarbonate, polyethylene, polypropylene, or polyoxymethylene.

5. The anatomical localization device of claim 1, wherein the indicator comprises barium sulfate, aluminum, stainless steel, titanium, gold, platinum, or tantalum.

6. An anatomical localization device comprising:
   an elongate handle configured for being grasped in a hand of a user proximate to a first end of the elongate handle;
   a marker assembly attached to a second end of the elongate handle and being configured for selective actuation for imparting a mark to skin of a subject, the marker assembly comprising plastic composite, such that the marker assembly is radiolucent;
   an indicator attached to the marker assembly, the indicator being radiopaque, wherein the indicator is configured for being radiographically visualized, wherein the elongate handle is configured for being manipulated by the user for motivating the marker assembly across an anatomical region of a subject being radiographically visualized for localizing the indicator over an anatomical target, enabling the user for selectively actuating the marker assembly for marking the skin over the anatomical target; and
   wherein the marker assembly comprises:
      a first tube;
      a second tube slidably attached to the first tube, such that an upper limit of the second tube is positioned within the first tube and a lower limit of the second tube is external to the first tube;
      a marking pen attached to and positioned substantially within the first tube, the marking pen extending into the second tube; and
      a biaser attached to the first tube and operationally engaged to the second tube, such that the second tube is biased to a first position, wherein the second tube extends from the first tube past a tip of the marking pen, wherein the second tube is configured for being pressed against skin over the anatomical target such that the second tube retracts into the first tube and the marking pen imparts a mark to the skin.

7. The anatomical localization device of claim 6, wherein the elongate handle extends substantially radially from the first tube.

8. The anatomical localization device of claim 6, further including:
   the first tube being internally threaded adjacent to an upper end of the first tube;
   a cap selectively threadedly attachable to the first tube for closing the upper end;
   a channel extending axially through the cap, the marking pen being circumferentially complementary to and positioned through the channel, such that the marking pen is frictionally attached to the cap;
   a first ring attached to and positioned within the first tube proximate to the upper end;
   a second ring attached to and extending radially from the upper limit of the second tube; and
   the biaser comprising a spring positioned in the first tube between the first ring and the second ring, wherein the spring is configured for tensioning upon pressing of the lower limit of the second tube against the skin of the subject and for rebounding upon lifting of the marker assembly from the skin.

9. The anatomical localization device of claim 6, wherein the first tube and the second tube are cylindrical.

10. The anatomical localization device of claim 6, wherein the indicator is attached to the lower limit of the second tube.

11. A radiographically guided method of marking a anatomical target comprising the steps of:
providing a radiographic imaging device;
providing an anatomical localization device comprising:
an elongate handle configured for being grasped in a hand of a user proximate to a first end of the elongate handle,
a marker assembly attached to a second end of the elongate handle and being configured for selective actuation for imparting a mark to skin of a subject, the marker assembly comprising plastic composite such that the marker assembly is radiolucent, the marker assembly being actuated in a linear direction by pressure on the marker assembly to produce the mark on the skin aligned with the direction of pressure applied to the marker assembly, and
an indicator attached to the marker assembly, the indicator being radiopaque, wherein the indicator is configured for being radiographically visualized, wherein the elongate handle is configured for being manipulated by the user for motivating the marker assembly across an anatomical region of a subject being radiographically visualized for localizing the indicator over an anatomical target, enabling the user for selectively actuating the marker assembly for marking the skin over the anatomical target;
positioning a subject for imaging by the radiographic imaging device;
grasping the elongate handle and positioning the marker assembly on the skin of the subject proximate to the anatomical target;
actuating the radiographic imaging device;
manipulating the elongate handle to position the indicator over the anatomical target; and
actuating the marker assembly to mark the skin over the anatomical target.

12. The method of claim 11, wherein the elongate handle comprises a plurality of nested sections, such that the elongate handle is selectively extensible.

13. The method of claim 12, wherein the plurality of nested sections comprises two nested sections.

14. The method of claim 11, wherein the marker assembly comprises polyetherimide, polycarbonate, polyethylene, polypropylene, or polyoxymethylene.

15. The method of claim 11, wherein:
the marker assembly comprises:
a first tube,
a second tube slidably attached to the first tube, such that an upper limit of the second tube is positioned within the first tube and a lower limit of the second tube is external to the first tube,
a marking pen attached to and positioned substantially within the first tube, the marking pen extending into the second tube, and
a biaser attached to the first tube and operationally engaged to the second tube, such that the second tube is biased to a first position, wherein the second tube extends from the first tube past a tip of the marking pen, wherein the second tube is configured for being pressed against skin over the anatomical target such that the second tube retracts into the first tube and the marking pen imparts a mark to the skin; and
the step of actuating the marker assembly comprises application of a force to the elongate handle to press the second tube against the skin of the subject, such that the second tube is retracted into the first tube and the tip of the marking pen contacts the skin over the anatomical target.

16. The method of claim 15, wherein the elongate handle extends substantially radially from the first tube.

17. The method of claim 15, further including:
the first tube being internally threaded adjacent to an upper end of the first tube;
a cap selectively threadedly attachable to the first tube for closing the upper end;
a channel extending axially through the cap, the marking pen being circumferentially complementary to and positioned through the channel, such that the marking pen is frictionally attached to the cap;
a first ring attached to and positioned within the first tube proximate to the upper end;
a second ring attached to and extending radially from the upper limit of the second tube; and
the biaser comprising a spring positioned in the first tube between the first ring and the second ring, wherein the spring is configured for tensioning upon pressing of the lower limit of the second tube against the skin of the subject and for rebounding upon lifting of the marker assembly from the skin.

18. The method of claim 15, wherein the first tube and the second tube are cylindrical.

19. The method of claim 15, wherein the indicator is attached to the lower limit of the second tube.

20. The method of claim 11, wherein the indicator comprises barium sulfate, aluminum, stainless steel, titanium, gold, platinum, or tantalum.

* * * * *